(12) United States Patent
Flick

(10) Patent No.: US 6,959,640 B2
(45) Date of Patent: Nov. 1, 2005

(54) DEVICE FOR MAGNETICALLY TREATING MATERIALS AND ASSOCIATED METHODS

(75) Inventor: Kenneth E. Flick, Douglasville, GA (US)

(73) Assignee: Omega Patents, L.L.C., Douglasville, GA (US)

( * ) Notice: Subject to any disclaimer, the term of this patent is extended or adjusted under 35 U.S.C. 154(b) by 237 days.

(21) Appl. No.: 10/368,704

(22) Filed: Feb. 18, 2003

(65) Prior Publication Data

US 2003/0228399 A1 Dec. 11, 2003

Related U.S. Application Data

(63) Continuation-in-part of application No. 10/164,750, filed on Jun. 6, 2002.

(51) Int. Cl.⁷ .............................. C02F 1/48; B01D 35/06; B03C 1/02; A21D 6/00
(52) U.S. Cl. ........................... 99/277.1; 99/275; 99/451; 210/695; 426/234; 426/237; 426/330.4
(58) Field of Search ................................ 99/275, 277.1, 99/451; 210/695, 222, 223; 426/237, 330.4, 592, 234, 238; 335/306, 303

(56) References Cited

U.S. PATENT DOCUMENTS

| | | | |
|---|---|---|---|
| 824,320 A | 6/1906 | Weitzmann | 426/237 |
| 3,831,743 A | 8/1974 | Leedy | 206/338 |
| 4,605,498 A | 8/1986 | Kulish | 210/222 |
| 4,872,401 A | 10/1989 | Lee | 99/275 |
| 4,888,113 A | 12/1989 | Holcomb | 210/222 |
| 4,895,650 A * | 1/1990 | Wang | 210/222 |
| 4,999,106 A | 3/1991 | Schindler | 210/222 |
| 5,113,751 A | 5/1992 | Holcomb et al. | 99/286 |
| 5,186,827 A * | 2/1993 | Liberti et al. | 210/222 |
| 5,248,437 A | 9/1993 | Forrest | 210/695 |
| 5,304,302 A | 4/1994 | Bossert | 210/222 |

(Continued)

FOREIGN PATENT DOCUMENTS

| | | |
|---|---|---|
| EP | 2702756 | 7/1978 |
| EP | 1 029 481 | 8/2000 |
| FR | 1 087 111 | 2/1955 |
| JP | 361125486 A | 6/1986 |
| JP | 362107752 A | 5/1987 |
| JP | 1148175 A | 6/1989 |
| JP | 1257473 A | 10/1989 |

OTHER PUBLICATIONS

Playboy Magazine, Oct. 1987, p. 184, "Magnetic Attraction".
Buy–A–Mag Company, Magnetic Cups, available at www.buyamag.com/cgi–bin/html/magnetic_cup.htm.
MagnetiCare, Rejuv Magnetic Liquid, available at www.rx-magnets.com.
Giovanni Cosmetics, Magnetic Energizing Shampoo, available at www.pacwestserv.com/haircare10.htm.

*Primary Examiner*—Reginald L. Alexander
(74) *Attorney, Agent, or Firm*—Allen, Dyer, Doppelt, Milbrath & Gilchrist, P.A.

(57) ABSTRACT

A device for magnetically treating materials includes a base, and at least one magnet carried by the base to generate a magnetic field within the material. In some embodiments, the material may be within a container, and the magnetic field may be generated within the container to magnetically treat the material. The material may be a beverage and the magnetic treatment may enhance the flavor of the beverage, or may be an emollient and the magnetic treatment may change a characteristic of the emollient. The device may include a base, a plurality of tubular members extending upwardly from the base and arranged in spaced-apart relation to receive the material, and at least one magnet within each of the tubular members to generate a magnetic field within the material.

47 Claims, 7 Drawing Sheets

U.S. PATENT DOCUMENTS

| | | | |
|---|---|---|---|
| 5,366,623 A | * 11/1994 | Clair | 210/222 |
| 5,500,121 A | 3/1996 | Thornton et al. | 210/222 |
| 5,556,654 A | 9/1996 | Fregeau | 426/234 |
| 5,571,481 A | 11/1996 | Powell et al. | 422/104 |
| 5,766,461 A | 6/1998 | Kämpf | 210/222 |
| 5,804,068 A | 9/1998 | Reed | 210/222 |
| 5,860,353 A | 1/1999 | Ceccarani | 99/277.1 |
| 5,891,331 A | 4/1999 | Yang | 210/222 |
| 5,942,161 A | 8/1999 | Pate | 261/91 |
| 6,022,479 A | 2/2000 | Smirnov | 210/695 |
| 6,287,614 B1 | 9/2001 | Peiffer | 426/237 |
| 6,305,656 B1 | 10/2001 | Wemyss | 248/309.4 |
| 6,319,913 B1 | 11/2001 | Mak et al. | 514/179 |
| 6,325,942 B1 | 12/2001 | Freije, III | 210/695 |
| 6,390,319 B1 | 5/2002 | Yu | 220/230 |

* cited by examiner

DEVICE FOR MAGNETICALLY TREATING MATERIALS AND ASSOCIATED METHODS

RELATED APPLICATIONS

The present application is a continuation-in-part of U.S. patent application Ser. No. 10/164,750 filed on Jun. 6, 2002, the entire disclosure of which is incorporated herein by reference.

FIELD OF THE INVENTION

The present invention relates to the field of magnetic treatment and, more particularly, to the field of magnetically treating materials to change properties thereof and associated methods.

BACKGROUND OF THE INVENTION

It is recognized that the flavor of some beverages may be enhanced by exposure to a magnetic field, which alters the molecular properties. U.S. Pat. No. 6,287,614 to Peiffer, for example, describes reducing the sensory perception of acids and tannins in alcoholic beverages by treating the beverage with a magnetic field. This treatment is asserted to give the alcoholic beverage a more aged flavor.

Accordingly, a number of products have been developed to expose beverages to magnetic fields to enhance flavor. Some of these products also attempt to enhance user convenience when magnetically treating beverages. For example, U.S. Pat. No. 4,872,401 to Lee discloses a container including surrounding sidewalls that have a plurality of magnets mounted on the inner side of the surrounding sidewalls to improve the flavor of fermented substances, such as wine, sauce, and tobacco. Another example is illustrated in U.S. Pat. No. 6,390,319 to Yu which discloses a beverage magnetizing container that exposes a beverage within the container to a magnetic field to promote preservation. The magnetic field is created by permanent magnets in the sidewalls, base, or cap of the container.

Other products magnetically treat beverages during initial processing. For example, U.S. Pat. No. 6,325,942 to Freije, III discloses a liquid treatment unit that includes a pipe having a plurality of magnets coupled thereto. The magnets treat liquid as it passes through the pipes. U.S. Pat. No. 5,860,353 to Ceccarani discloses an apparatus for accelerating the aging of alcoholic beverages. The apparatus exposes beverages to low-frequency polarized pulsating magnetic fields.

One shortcoming with several of these devices is that the container with its integral magnets must contact the beverage to be treated. In other words, the user must pour the beverage to be treated into the specialized container for treatment prior to consuming the beverage. These specialized containers may increase the cost of magnetically treating beverages and may also decrease consumer flexibility.

Emollients or other skin care or cosmetic materials are generally used to soothe or soften skin. More particularly, some emollients, such as lotions and creams, are used on a daily basis to moisturize skin, preventing dryness and chapping. Some climates, such as cold and/or dry environments, require the use of emollients more often than others, such as warm and/or humid environments.

Some emollients are dispensed from a container, into the hands of the user, and thereafter spread out into the skin of the user. In some situations, however, these emollients may leave the user's hands feeling oily, or greasy, so that it may be difficult for the user to use their hands after completing application of the emollient. Uniform coverage of the skin may also be difficult.

SUMMARY OF THE INVENTION

In view of the foregoing background, it is therefore an object of the present invention to provide a device and methods for enhancing properties of materials by exposure to a magnetic field.

This and other objects, advantages, and features of the present invention are provided by a device for magnetically treating material comprising a base, a plurality of tubular members extending upwardly from the base and arranged in spaced-apart relation to receive the material, and at least one magnet within each of the tubular members to generate a magnetic field within the material.

The tubular members may be arranged along points of an imaginary cylinder and may be at least three in number. The base may have a generally polygonal shape, and the tubular members may be positioned adjacent respective vertices of the polygonally shaped base. In some embodiments, the polygonal shape may be a square, and in other embodiments, the polygonal shape may be an equilateral triangle, for example.

In some embodiments, the tubular members may be fixed to the base. More particularly, the base and the tubular members may be integrally formed as a monolithic unit.

In other embodiments, the tubular members may be slidably positioned on the base to facilitate repositioning thereof. The base may have elongated slots formed therein to slidably receive respective ends of the tubular members. Further, each slot and respective end may form an elongated dovetail joint.

The base and the tubular members may comprise non-magnetic material, such as plastic, for example. Further, the magnets may comprise neodymium for a compact source of a strong magnetic field.

In some applications, the device may be used to enhance flavor of beverages, for example. In other applications, the device may be used to change characteristics, such as absorption, of emollient. Accordingly, one method aspect of the invention is for enhancing beverage flavor and may include providing a device comprising a base, a plurality of spaced-apart tubular members extending upwardly from the base, and at least one magnet within each of the tubular members, and positioning a container on the base and between the spaced-apart tubular members to expose a beverage in the container to a magnetic field to thereby enhance beverage flavor.

Another method aspect of the invention is for changing characteristics of an emollient. The method may comprise positioning a magnet adjacent the emollient to expose the emollient to a magnetic field to change the characteristics of the emollient.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and double prime notation are used to indicate similar elements in alternate embodiments.

Figure 1:
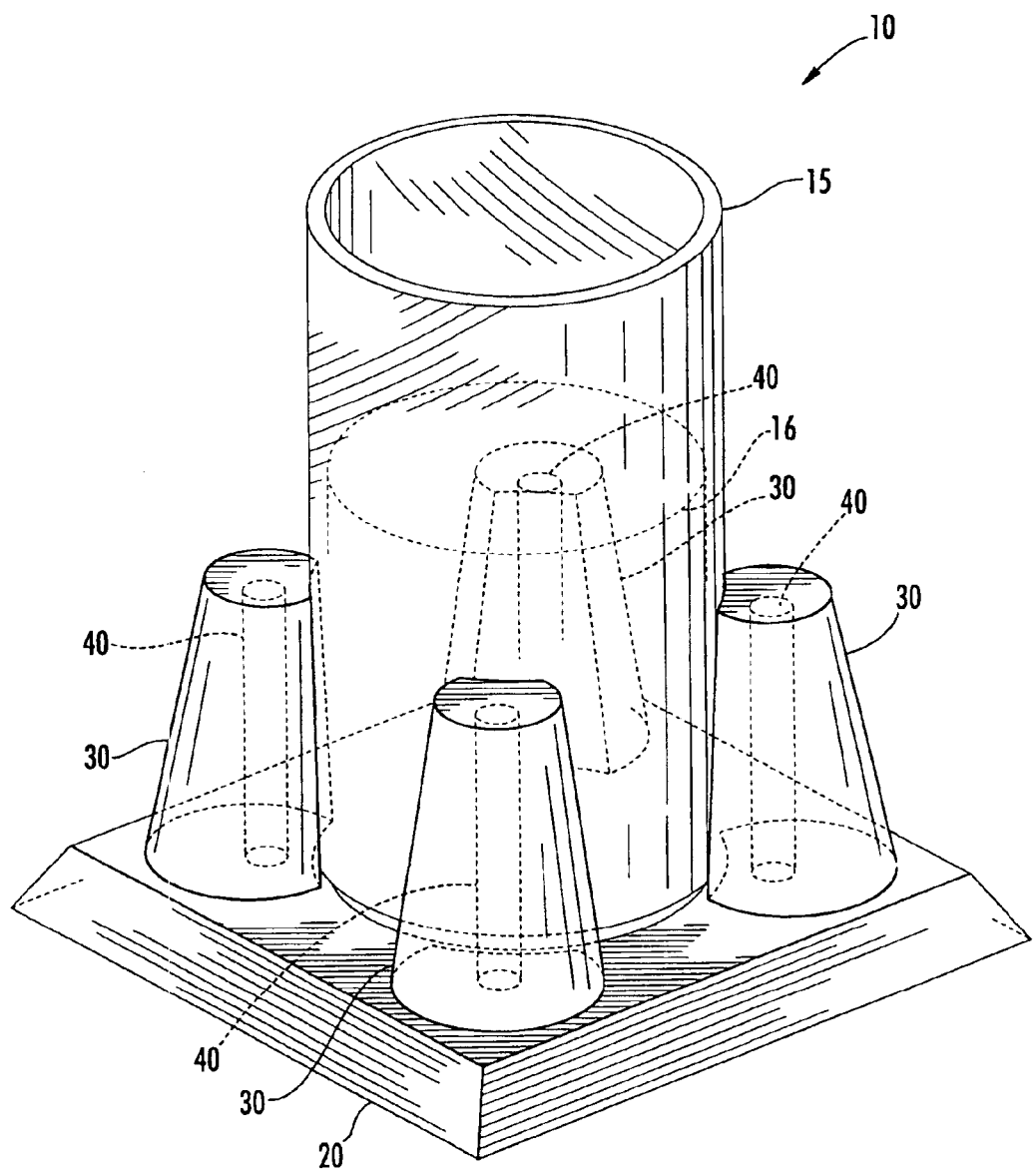
FIG. 1 is a perspective view of a device for magnetically treating material according to the present invention.
Figure 2:
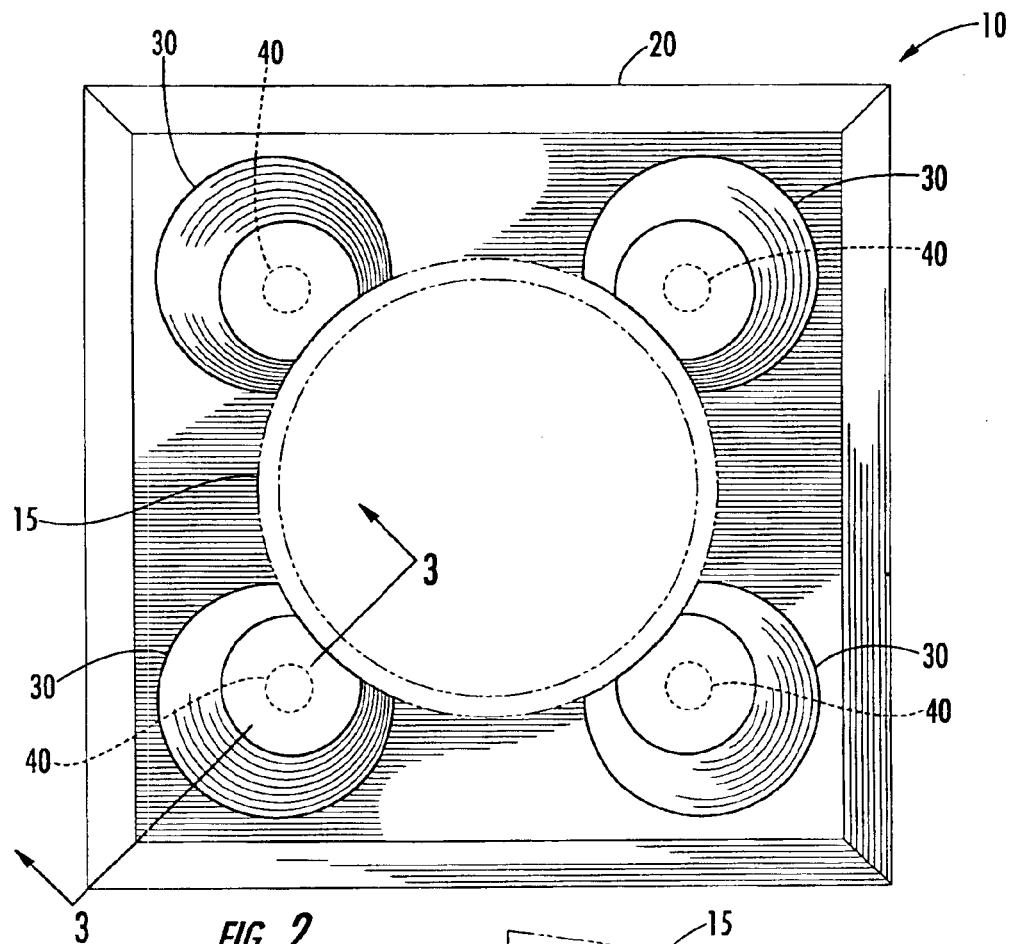
FIG. 2 is a top plan view of the device shown in FIG. 1.
Figure 3:
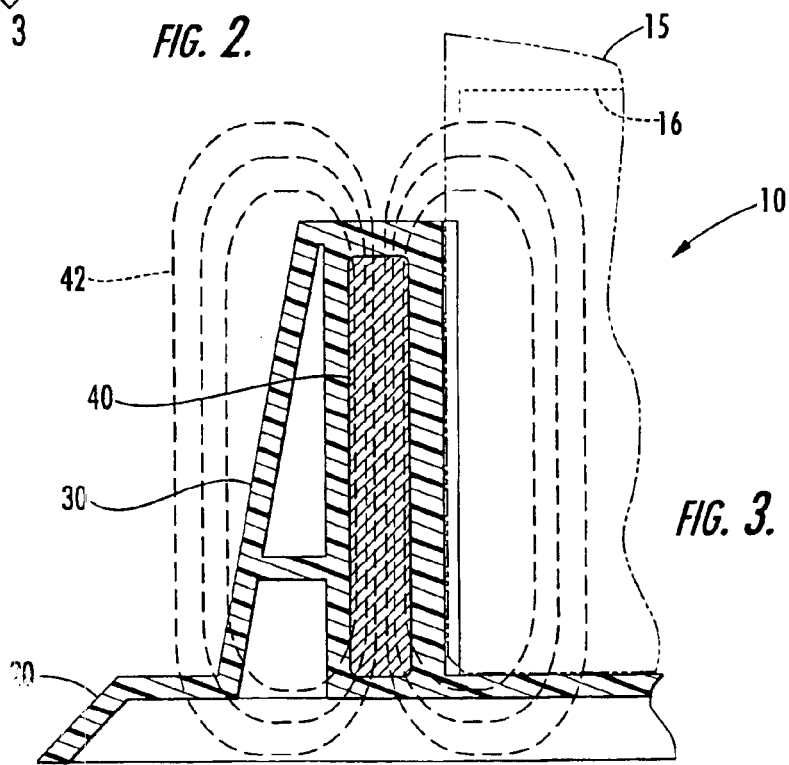
FIG. 3 is a cross-sectional view of the device taken along line 3—3 in FIG. 2.

Referring initially to FIGS. 1–3, a device 10 for magnetically treating material is now described. It will be readily understood by those skilled in the art that the material may be a beverage, or an emollient, for example, or any other type of material as will be discussed in greater detail below. It will also be understood by those skilled in the art that the material may be treated within a container 15, as illustrated, or, alternately, may be treated after it has been dispensed from the container.

The device 10 illustratively includes a base 20 and a plurality of tubular members 30 extending upwardly from the base. The tubular members 30 are arranged in spaced-apart relation to illustratively receive a container 15 therebetween when the container is positioned on the base 20.

The device 10 also includes a permanent magnet 40 within each of the tubular members 30 to illustratively generate a magnetic field 42 within the container 15 and, more particularly, within the material 16 in the container. Although the illustrated embodiment shows the magnetic field 42 being generated within the container 15, it shall be understood by those skilled in the art that the device 10 may be used to change characteristics of the material 16 by exposing the material to the magnetic field 42 after it has been dispensed from the container. For example, the device 10 may be used to treat emollient initially applied onto the hand of the user.

With respect to magnetically treating emollients, the characteristics of the emollient that may be changed, for example, include skin absorption and texture. An increase in skin absorption of the emollient may include an increase in the rate of skin absorption of the emollient into the skin of the user, for example. Also for example, an increase in skin absorption may include an increase in the amount of emollient that may be absorbed into the skin, as understood by those skilled in the art. Increasing skin absorption advantageously decreases a greasy, or oily, feel of an emollient, which may persist for some time after application, especially for emollients including lanolin.

It will be readily understood by those skilled in the art that an emollient may include any substance applied to the skin or hair for soothing or moisturizing purposes, for example. The emollient may, for example, be in the form of skin lotion, cream, cosmetic lotion, lip balm, lipstick, body washes, soaps, masks, cuticle oils, face care products, and hair care products, such as shampoos and conditioners, or any other type of emollient as will be understood by those skilled in the art.

The container 15 may, for example, be a plastic container, bottle, or any other non-ferrous container that permits the external magnetic field 42 to penetrate therethrough and into the material 16. The device 10 could be sized to treat material 16 in any type of container, as understood by those skilled in the art. In cases where the device 10 is used to magnetically treat a beverage, the container 15 may, for example, be a shot glass, or any other non-ferrous container that permits the external magnetic field 42 to penetrate into the beverage.

In such embodiments, the device 10 could be sized for a standard 12-ounce aluminum can, a wine bottle, a liquor bottle, a juice box, a milk carton, or any other type of beverage container as understood by those skilled in the art. In these embodiments, the device 10 may be used to enhance the flavor of alcoholic beverages, but may also be used to enhance the flavor of citrus juice and dairy products, for example. It will be understood by those skilled in the art that a beverage includes any liquid consumable substance, such as the above-referenced citrus juice, dairy products, and alcoholic beverages as well as sauces and soups, for example.

The tubular members 30 are illustratively arranged along points of an imaginary cylinder, such as sized to receive the container 15. In the illustrated embodiment, the tubular members 30 are fixed to the base 20. The tubular members 30 are illustrated as having a frusto-conical shape wherein an end having a larger diameter is positioned adjacent the base 20. Each of the tubular members 30 also illustratively includes a recess formed therein to receive arcuate portions of the container 15. The tubular members 30 can have other interior and exterior shapes as well. For example, the shapes may be oval, elliptical, generally polygonal, square, triangular, hexagonal, octagonal, rectangular, etc. as will be appreciated by those skilled in the art.

The base 20 and the tubular members 30 are integrally formed as a monolithic unit in some embodiments. Each of the tubular members 30 illustratively includes a permanent magnet 40 therein. The permanent magnet 40 may be a plurality of permanent magnets. A magnetic field 42 is created by the permanent magnets 40 so that the emollient 16 is exposed to the magnetic field when positioned between the tubular members 30.

The base 20 and the tubular members 30 may comprise nonmagnetic material, such as plastic material, for example. It will be understood by those skilled in the art that any nonmagnetic material may be used to form the base 20 and tubular members 30 of the device 10. The permanent magnets 40 preferably comprise neodymium, but may be provided by any magnetic material, such as a ceramic block magnet, alnico, and samarium cobalt, as understood by those skilled in the art. Electromagnets could be used in some embodiments, as will be appreciated by those skilled in the art.

The base 20 illustratively has a generally polygonal shape. The polygonal shape in the embodiment illustrated in FIGS. 1–3, for example, is square. In other embodiments, the base 20 may include other polygonal shapes as understood by those skilled in the art.

Figure 4:
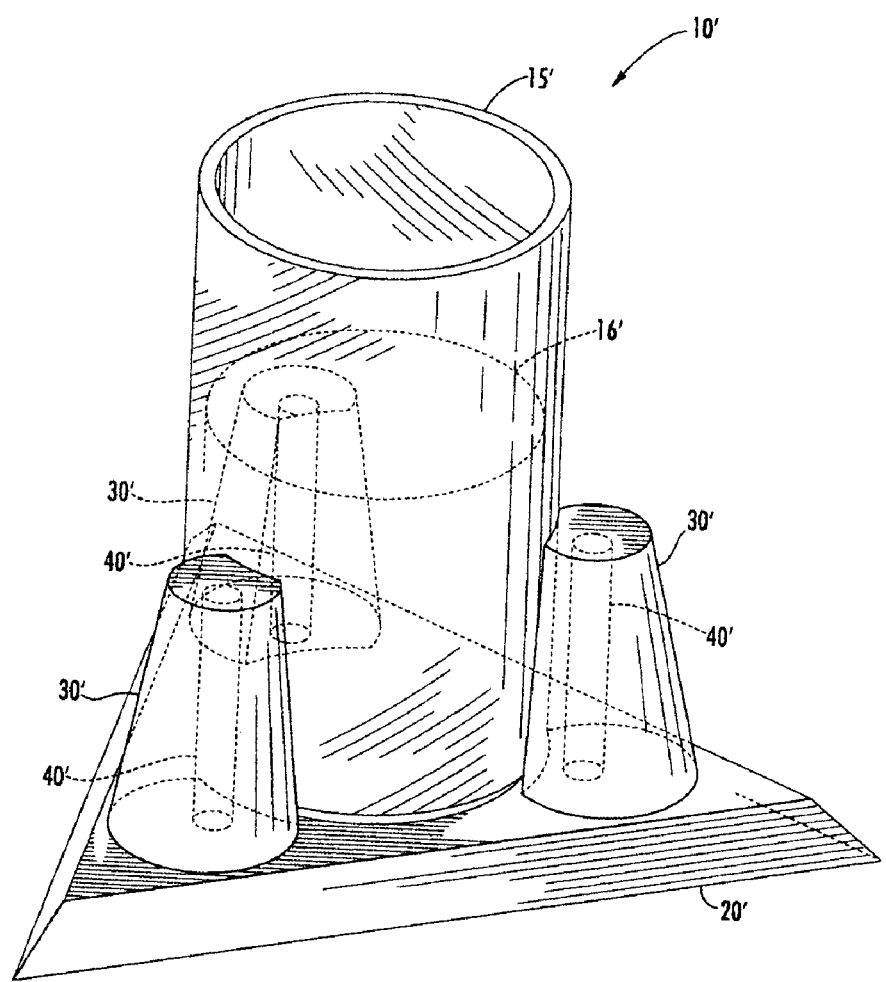
FIG. 4 is a perspective view of another embodiment of the device for magnetically treating material according to the present invention.
Figure 5:
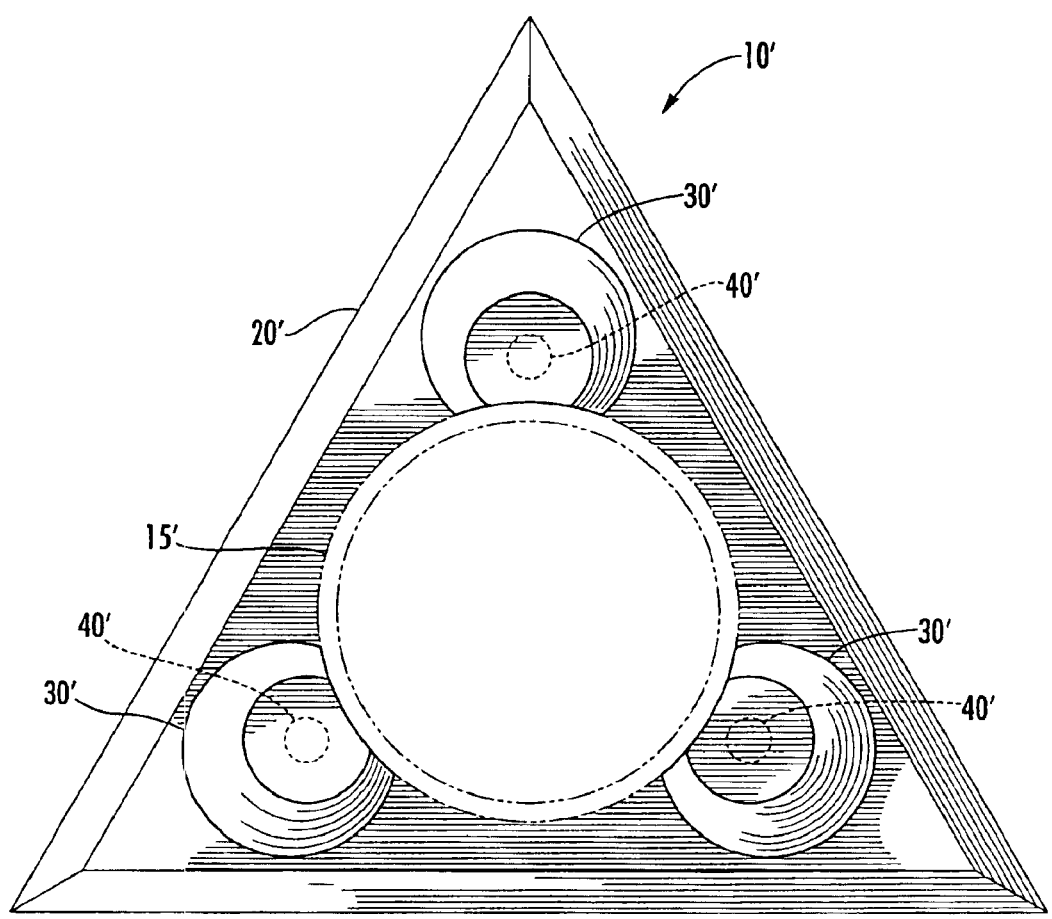
FIG. 5 is a top plan view of the device shown in FIG. 4.
Figure 6:
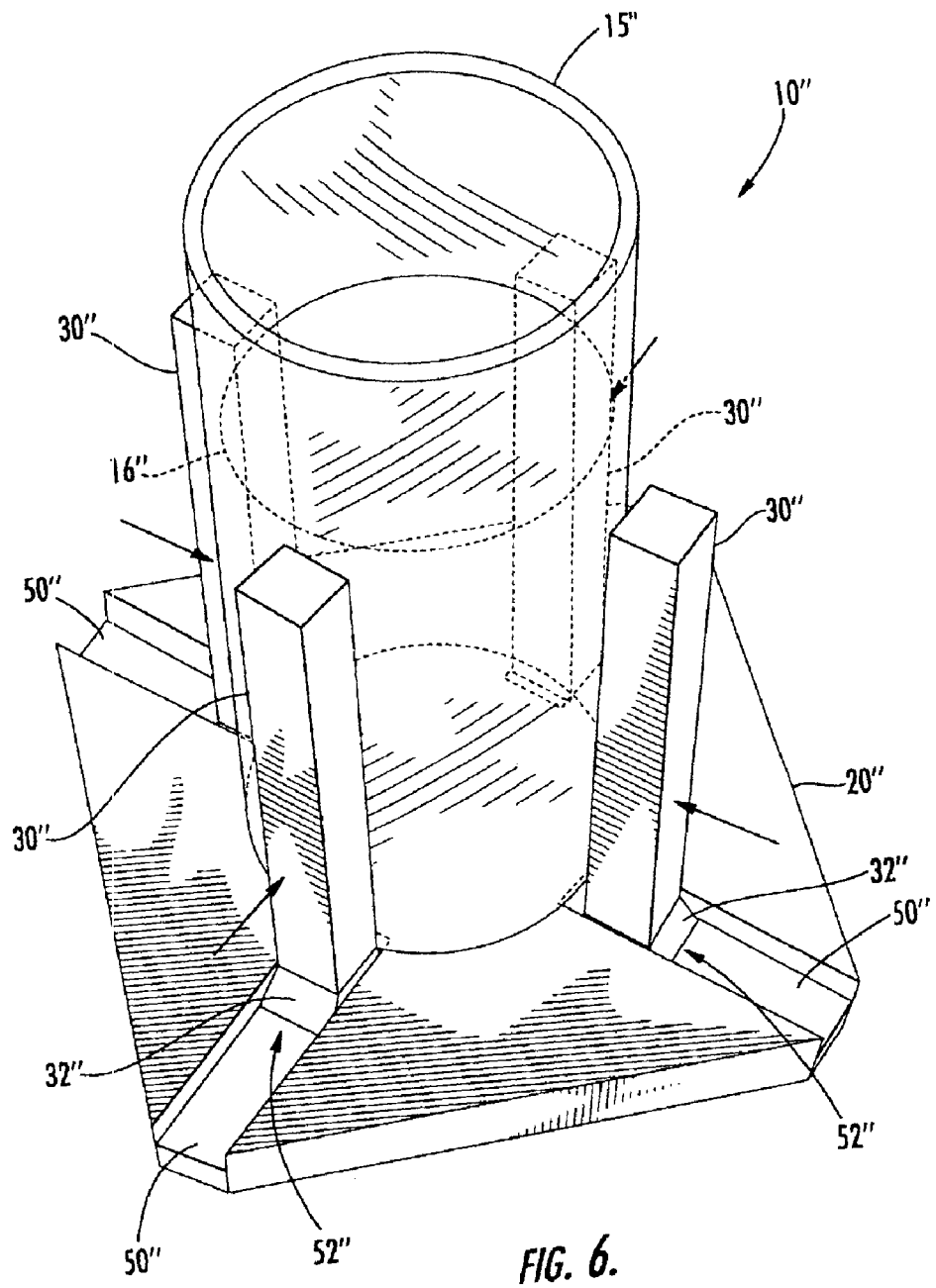
FIG. 6 is a perspective view of yet another embodiment of the device for magnetically treating material according to the present invention.
Figure 7:
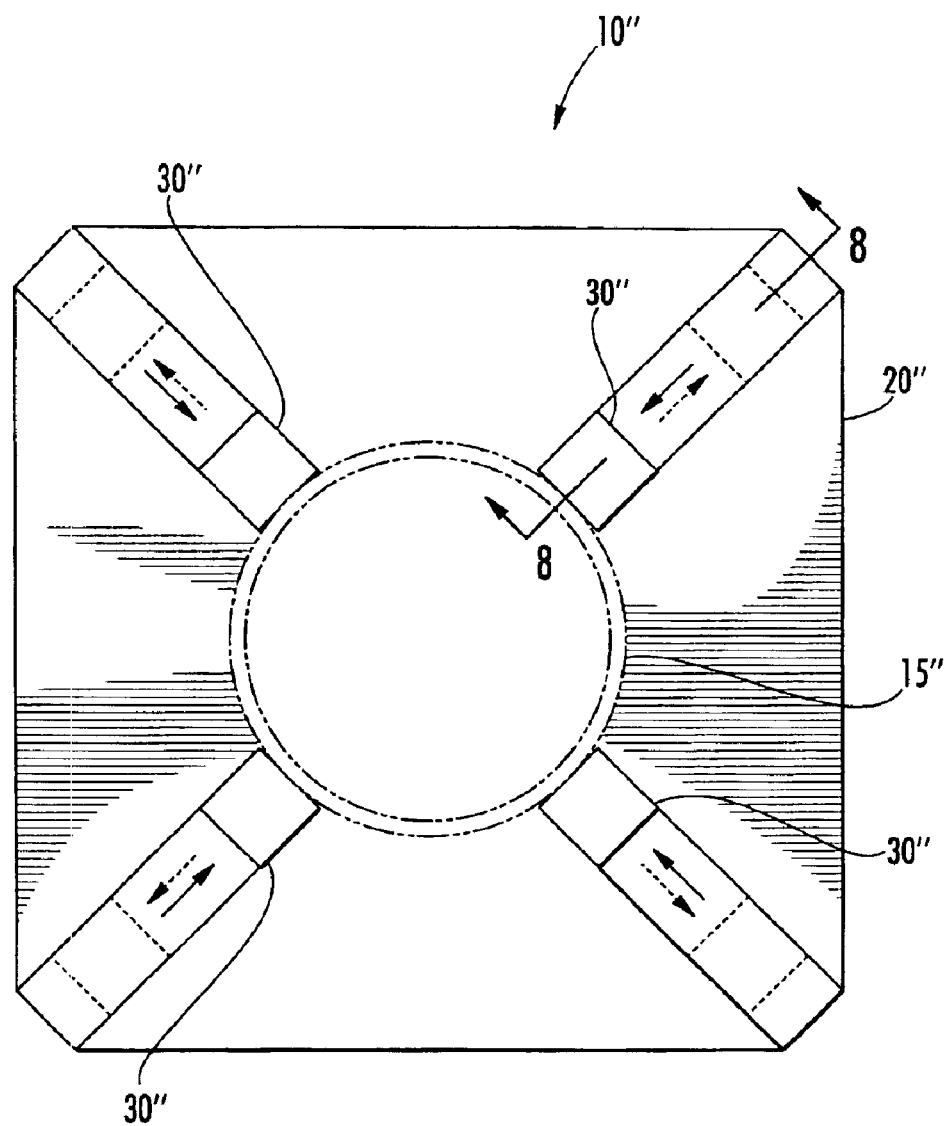
FIG. 7 is a top plan view of the device shown in FIG. 6.
Figure 8:
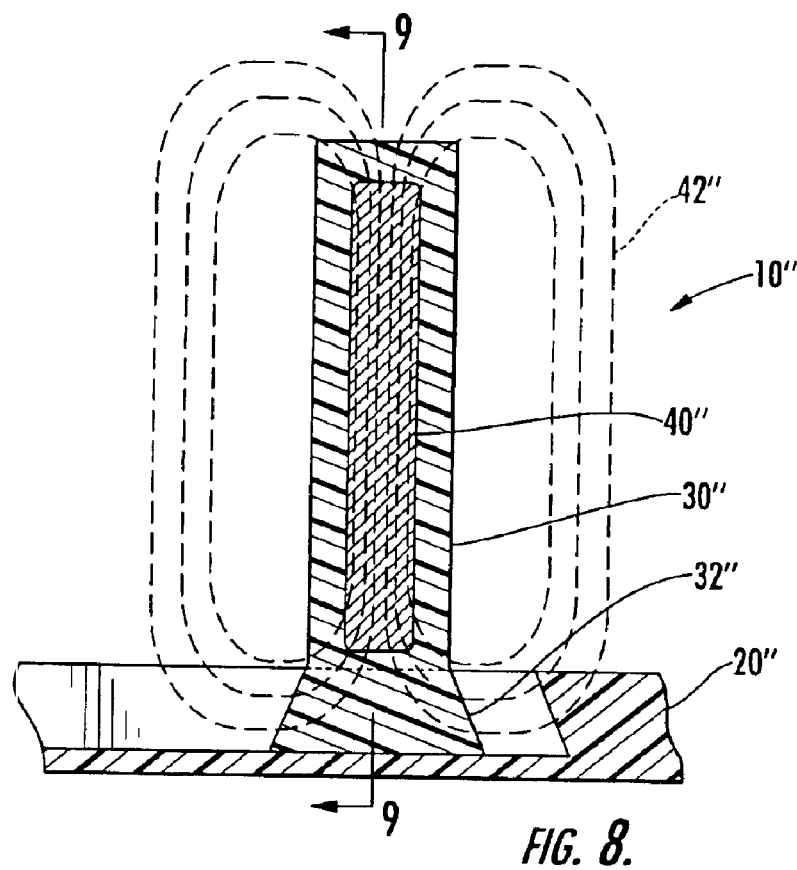
FIG. 8 is a cross-sectional view of the device taken along line 8—8 in FIG. 7.
Figure 9:
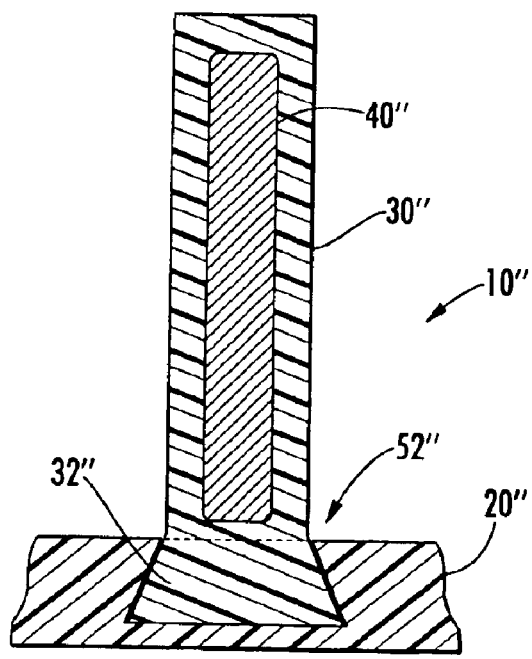
FIG. 9 is a cross-sectional view of a tubular member of the device taken along line 9—9 in FIG. 8.

Turning now to FIGS. 4–5, another embodiment of the device 10' is now described. The tubular members 30' illustratively comprise three tubular members and are positioned adjacent respective vertices of the triangularly shaped base 20'. A permanent magnet 40' is positioned within each of the tubular members 30' to create a magnetic field 42' to treat material 16'. In this embodiment of the device 10', the polygonal shape of the base 20' is an equilateral triangle. In applications in which the material 16' is treated within the container 15', the container 15' may fit closely within the tubular members 30', as in the illustrated embodiment. The container 15' may, however, be smaller in diameter while the material 16' positioned therein still experiences the treating effects caused by the magnetic field 42' from the permanent magnets 40'.

Turning now additionally to FIGS. 6–9, yet another embodiment of the device 10" is now described. In this embodiment, the tubular members 30" are illustratively slidably positioned on the base 20" to facilitate repositioning thereof. This embodiment is especially advantageous when treating material 16" in a container 15". The base 20" illustratively includes elongated slots 50" formed therein to slidably receive respective ends 32" of the tubular members 30". Each slot 50" and respective end 32" illustratively form an elongated dovetail joint 52" to thereby enhance the security of the tubular members 30" within the slots.

In this embodiment of the device 10" the tubular members 30" are illustratively slidable between extended and retracted positions and, more particularly, between an infinite number of positions between the extended and retracted positions. When positioned toward the extended positions, the tubular members 30" are configured to receive a larger container 15" than when positioned toward the retracted positions. For example, when positioned toward the extended positions, a large container carrying a great amount of emollient may be readily positioned between the tubular members 30". Also for example, when positioned toward the retracted position, a rather small container 15", such as a container suitable for lipstick, or lip-gloss, for example, may be readily positioned between the tubular members 30". In the case of magnetically treating a beverage, the small container may, for example, be a shot glass, while a large container may be a liquor or wine bottle, for example. This advantageously allows a user to treat material 16" in any one of a number of different sized containers 15".

One method aspect of the present invention is for changing characteristics of an emollient. The method comprises positioning a magnet 40, 40', 40" adjacent the emollient to expose the emollient to a magnetic field to change the characteristics of the emollient when thereafter applied to skin of a user, or when initially dispensed into the user's hand. The changed characteristic may, for example, be the texture of the emollient or, as described in detail above, the skin absorption of the emollient.

In some embodiments, the method may comprise providing a device 10, 10', 10" including a base 20, 20', 20" a plurality of spaced-apart tubular members 30, 30', 30" extending upwardly from the base and at least one magnet 40, 40', 40" within each of the tubular members. The method also includes positioning a container 15, 15', 15" on the base 20, 20', 20" and between the spaced-apart tubular members 30, 30', 30" to expose the emollient 16, 16', 16" in the container to a magnetic field to increase skin absorption of the emollient. In other embodiments as shown in FIGS. 6–9, the method also includes slidably positioning the tubular members 30" on the base 20" to accommodate a size of the container 15".

Another method aspect of the present invention is for enhancing beverage flavor. The method comprises providing a device 10, 10', 10" including a base 20, 20', 20" a plurality of spaced-apart tubular members 30, 30', 30" extending upwardly from the base 20, 20', 20" and at least one magnet 40, 40', 40" within each of the tubular members. The method also includes positioning a container 15, 15', 15" on the base and between the spaced-apart tubular members to expose a beverage in the container to a magnetic field to thereby enhance beverage flavor. In some embodiments as shown in FIGS. 6–9, the method also includes slidably positioning the tubular members 30" on the base 20" to accommodate a size of the container 15".

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A device for magnetically treating material in a container, the device comprising:
    a base;
    at least three tubular members extending upwardly from said base and arranged in spaced-apart relation to define at least three points on said base receive the material in the container therebetween; and
    at least one magnet within each of said tubular members to generate a corresponding plurality of magnetic fields within the material.

2. A device according to claim 1 wherein said base has a generally polygonal shape; and wherein said tubular members are positioned adjacent respective vertices of the polygonally shaped base.

3. A device according to claim 2 wherein said polygonal shape comprises a square.

4. A device according to claim 2 wherein said polygonal shape comprises an equilateral triangle.

5. A device according to claim 1 wherein said tubular members are fixed to said base.

6. A device according to claim 5 wherein said base and said tubular members are integrally formed as a monolithic unit.

7. A device according to claim 1 wherein said tubular members are slidably positioned on said base to facilitate repositioning thereof.

8. A device according to claim 7 wherein said base has elongated slots formed therein to slidably receive respective ends of said tubular members.

9. A device according to claim 8 wherein each slot and respective end form an elongated dovetail joint.

10. A device according to claim 1 wherein said base and said tubular members comprise non-magnetic material.

11. A device according to claim 1 wherein said base and said tubular members comprise plastic.

12. A device according to claim 1 wherein said magnets comprise neodymium.

13. A device according to claim 1 wherein said tubular members are arranged along points of an imaginary cylinder.

14. A device for magnetically treating material in a container, the device comprising:
    a base;
    at least three tubular members integrally formed with said base and extending upwardly therefrom, said tubular members arranged in spaced-apart relation to define at least three points on said base to receive the material in the container therebetween; and at least one permanent magnet within each of said tubular members to generate a corresponding plurality of magnetic fields within material.

15. A device according to claim 14 wherein said base has a generally polygonal shape; and wherein said tubular members are positioned adjacent respective vertices of the polygonally shaped base.

16. A device according to claim 15 wherein said polygonal shape comprises a square.

17. A device according to claim 15 wherein said polygonal shape comprises an equilateral triangle.

18. A device according to claim 14 wherein said base and said tubular members comprise non-magnetic material.

19. A device according to claim 14 wherein said base and said tubular members comprise plastic.

20. A device according to claim 14 wherein said at least one permanent magnet comprises neodymium.

21. A device according to claim 14 wherein said tubular members are arranged along points of an imaginary cylinder.

22. A device for magnetically treating material in a container, the device comprising:
   a base;
   at least three tubular members extending upwardly from said base and arranged in spaced-apart relation to define at least three points on said base to receive the material in the container therebetween;
   said tubular members slidably positioned on said base to facilitate repositioning thereof; and
   at least one permanent magnet within each of said tubular members to generate a corresponding plurality of magnetic fields within material.

23. A device according to claim 22 wherein said base has a generally polygonal shape; and wherein said tubular members are positioned adjacent respective vertices of the polygonally shaped base.

24. A device according to claim 22 wherein said polygonal shape comprises a square.

25. A device according to claim 22 wherein said polygonal shape comprises an equilateral triangle.

26. A device according to claim 22 wherein said base has elongated slots formed therein to slidably receive respective ends of said tubular members.

27. A device according to claim 26 wherein each slot and respective end form an elongated dovetail joint.

28. A device according to claim 22 wherein said base and said tubular members comprise non-magnetic material.

29. A device according to claim 22 wherein said base and said tubular members comprise plastic.

30. A device according to claim 22 wherein said at least one permanent magnet comprises neodymium.

31. A device according to claim 22 wherein said tubular members are arranged along points of an imaginary cylinder.

32. A method for enhancing beverage flavor comprising:
   providing a device comprising a base, a plurality of spaced-apart tubular members extending upwardly from the base to define an imaginary cylinder therebetween, and at least one magnet within each of the tubular members; and
   positioning a container on the base and between the spaced-apart tubular members to expose a beverage in the container to a correspondingly plurality of magnetic fields to thereby enhance beverage flavor.

33. A method according to claim 32 wherein the tubular members are slidably positioned on the base; and further comprising slidably positioning the tubular members on the base to accommodate a size of the container.

34. A method according to claim 32 wherein the beverage comprises a dairy product beverage.

35. A method according to claim 32 wherein the beverage comprises an alcoholic beverage.

36. A method according to claim 32 wherein the beverage comprises a citrus juice beverage.

37. A method according to claim 32 wherein the tubular members are at least three in number.

38. A method for changing characteristics of an emollient, the method comprising:
   providing a device comprising a base, a plurality of spaced-apart tubular members extending upwardly from the base to define an imaginary cylinder therebetween, and at least one magnet within each of the tubular members; and
   positioning a container on the base and between the plurality of spaced-apart tubular members to expose the emollient in the container to a corresponding plurality of magnetic fields to change the characteristics of the emollient.

39. A method according to claim 38 wherein the base and the plurality of spaced-apart tubular members are integrally formed as a monolithic unit.

40. A method according to claim 38 further comprising slidably positioning the plurality of tubular members on the base.

41. A device for magnetically treating material in a container, the device comprising:
   a base;
   at least three elongate members extending upwardly from said base and arranged in spaced-apart relation to define at least three points on said base to receive the material in the container therebetween; and
   at least one magnet carried by each of said elongate members to generate a corresponding plurality of magnetic fields within the material.

42. A device according to claim 41 wherein said base has a generally polygonal shape; and wherein said elongate members are positioned adjacent respective vertices of the polygonally shaped base.

43. A device according to claim 41 wherein said elongate members are fixed to said base.

44. A device according to claim 43 wherein said base and said elongate members are integrally formed as a monolithic unit.

45. A device according to claim 41 wherein said elongate members are slidably positioned on said base to facilitate repositioning thereof.

46. A device according to claim 45 wherein said base has elongated slots formed therein to slidably receive respective ends of said elongate members.

47. A device according to claim 46 wherein each slot and respective end form an elongated dovetail joint.

* * * * *

UNITED STATES PATENT AND TRADEMARK OFFICE
CERTIFICATE OF CORRECTION

PATENT NO. : 6,959,640 B2  
DATED : November 1, 2005  
INVENTOR(S) : Flick

It is certified that error appears in the above-identified patent and that said Letters Patent is hereby corrected as shown below:

Column 6,
Line 25, delete "base receive" insert -- base to receive --.

Signed and Sealed this

Second Day of May, 2006

JON W. DUDAS
*Director of the United States Patent and Trademark Office*